United States Patent [19]

Jezuit et al.

[11] Patent Number: 4,728,381
[45] Date of Patent: Mar. 1, 1988

[54] MACHINE AND METHOD FOR MANUFACTURING A DISPOSABLE ABSORBENT CONTINENCE PAD

[75] Inventors: Arthur D. Jezuit, Wood Dale; Richard M. Oldendorf, Westmont, both of Ill.

[73] Assignee: Hooper, Inc., Itasca, Ill.

[21] Appl. No.: 861,859

[22] Filed: May 12, 1986

[51] Int. Cl.⁴ .................. A61F 13/18; B29C 51/08; B29C 51/20; B32B 31/08

[52] U.S. Cl. .................. 156/245; 156/252; 156/292; 156/500; 156/510; 156/553; 83/614; 83/620; 264/511; 264/550; 264/551; 264/554; 425/291; 425/292; 425/125; 425/519; 425/388; 425/395; 425/398; 428/136; 604/372

[58] Field of Search .......... 604/372; 83/614, 620; 156/211, 270, 553, 245, 292, 500, 510, 252, 257; 425/80.1, 83.1, 519, 290, 291, 292, 297, 125, 388, 395, 398, 399; 428/134, 135, 136; 264/511, 550, 551, 554

[56] References Cited

U.S. PATENT DOCUMENTS

| | | | |
|---|---|---|---|
| 2,800,423 | 7/1957 | DeSwart | 428/136 |
| 3,397,507 | 8/1968 | Myers | 53/112 |
| 3,444,665 | 5/1969 | Prena | 53/112 |
| 3,477,317 | 11/1969 | Liander | 83/620 |
| 3,706,174 | 12/1972 | Young et al. | 53/112 |
| 4,119,450 | 10/1978 | Bianco | 156/276 |
| 4,342,183 | 9/1982 | Gordon et al. | 264/550 |
| 4,516,461 | 5/1985 | Schaeffer | 83/614 |
| 4,636,349 | 1/1987 | MacLaughlin | 264/550 |

FOREIGN PATENT DOCUMENTS 972662 10/1964 United Kingdom ............... 264/551

Primary Examiner—Jerome Massie
Assistant Examiner—Lori Cuerva
Attorney, Agent, or Firm—Wood, Dalton, Phillips, Mason & Rowe

[57] ABSTRACT

A machine and method for manufacturing a disposable absorbent continence pad. The machine has a series of stations including a shell-forming station for forming a shell from thermoplastic material, a slitting station for forming slits in a facing material to be sealed to a shell in order to permit the facing material to adapt to the shape of the shell and a sealing station where the facing material and the shell are heat sealed together. The shell-forming station, slitting station and sealing station have special components to assure accurate molding of the shell and prevent wrinkles in the facing material. The manufacturing method embodies a series of processing steps as carried out at the aforesaid stations.

13 Claims, 18 Drawing Figures

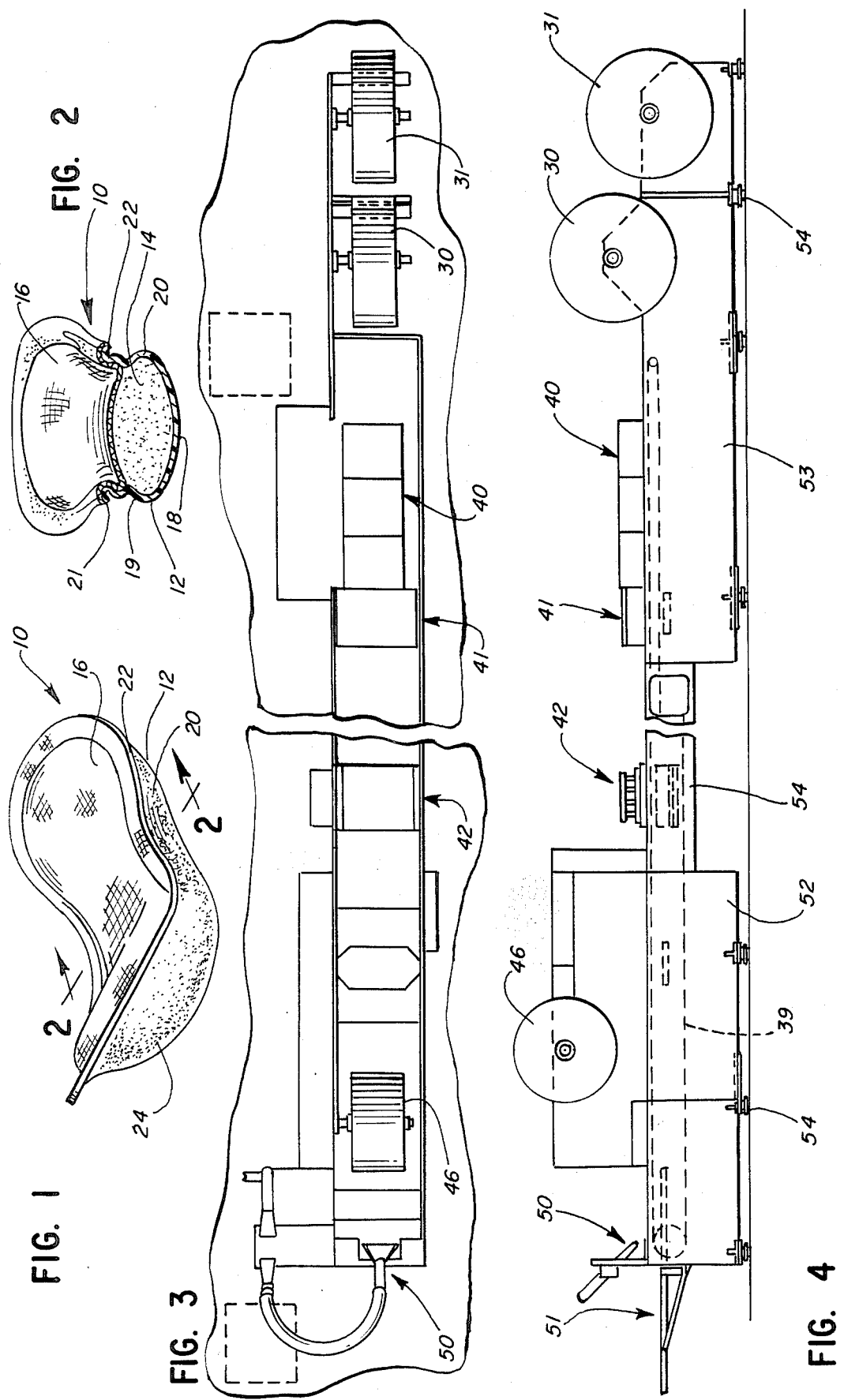

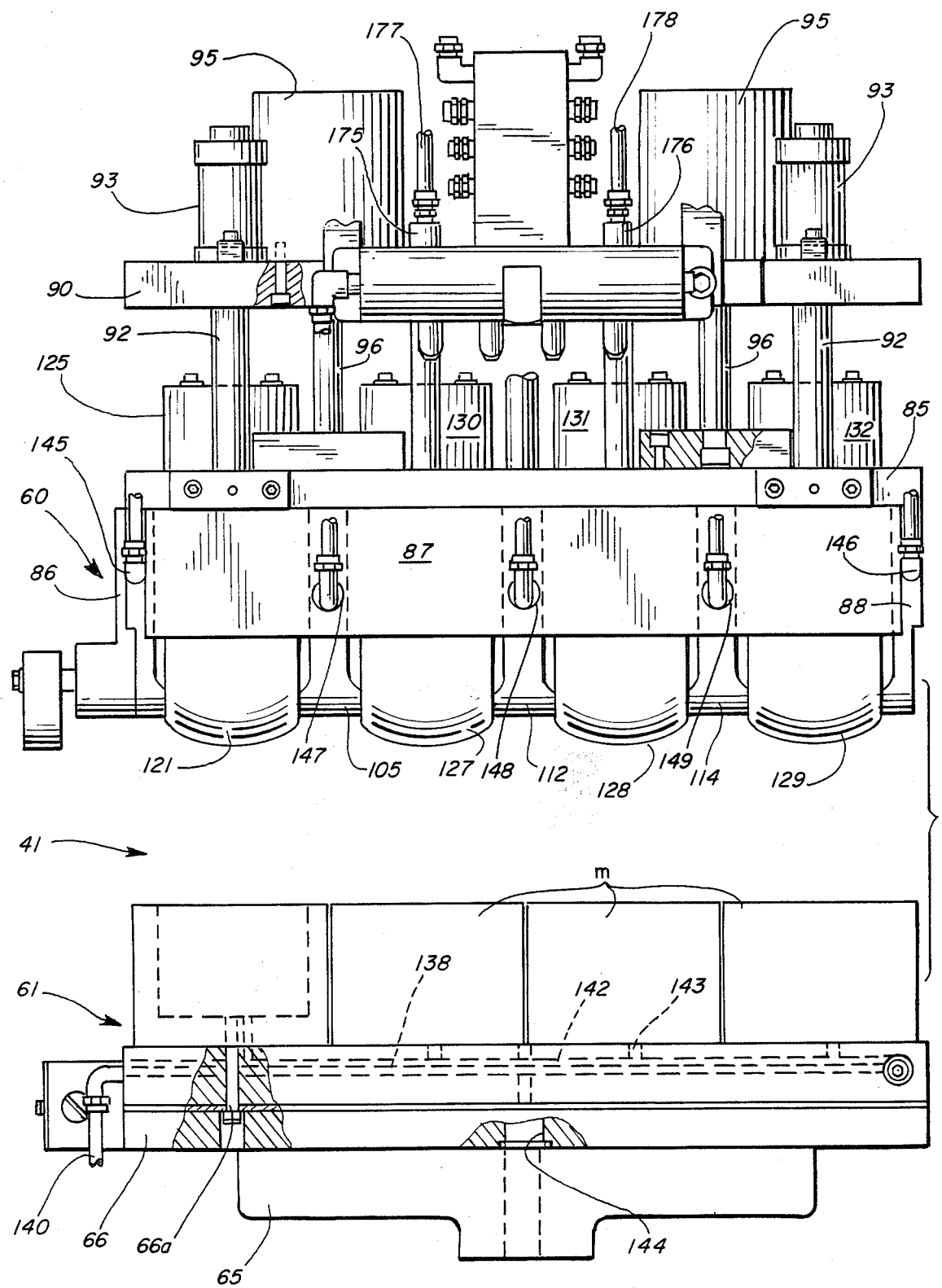

U.S. Patent  Mar. 1, 1988  Sheet 5 of 10  4,728,381
FIG. 7
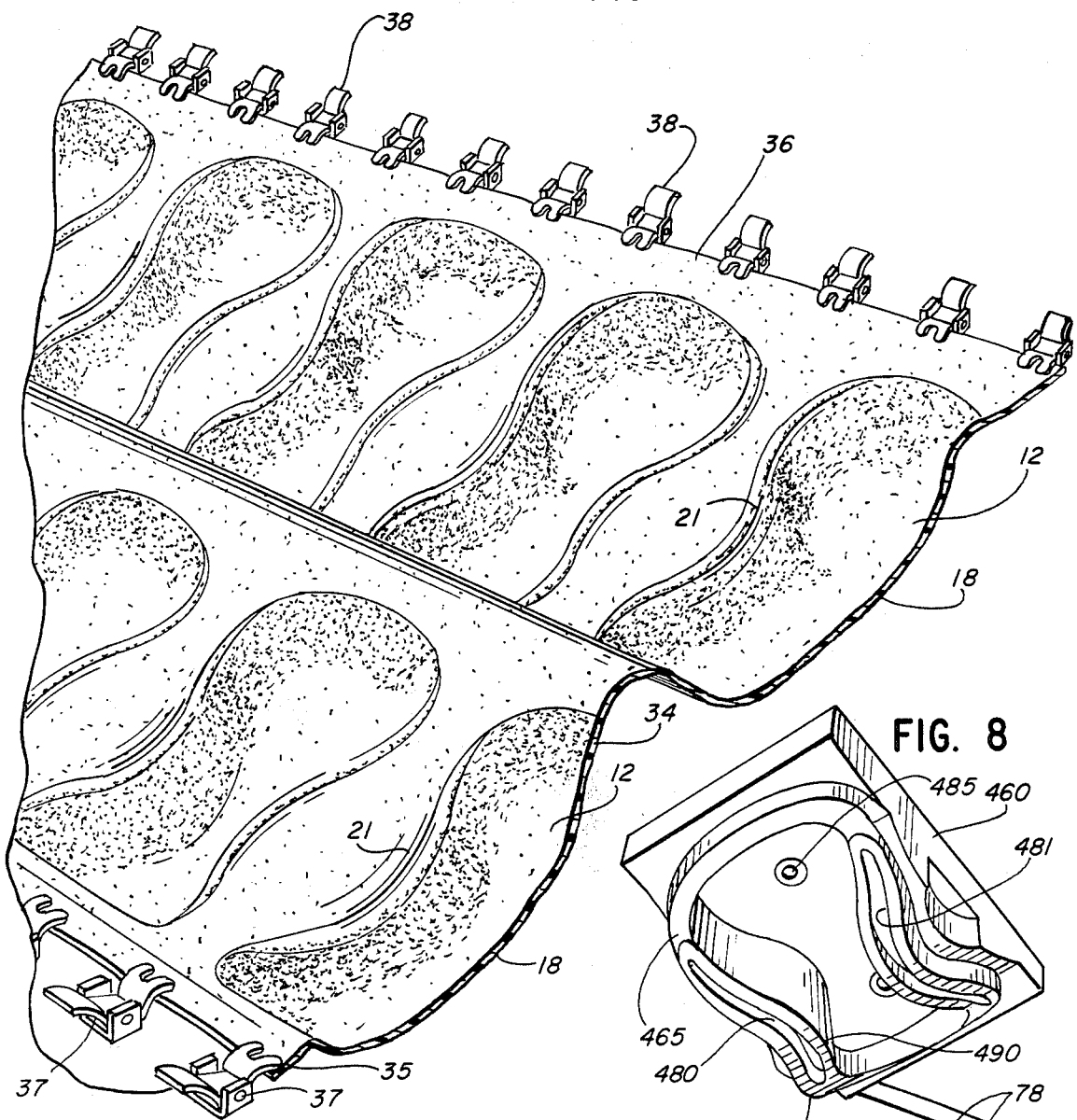
FIG. 8
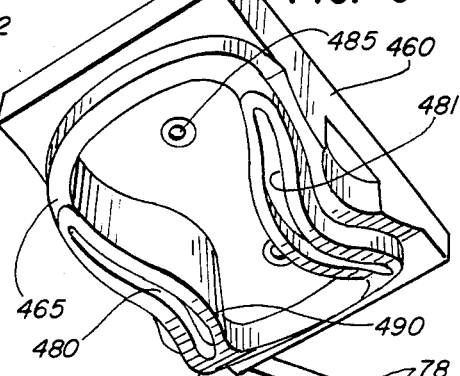
FIG. 9
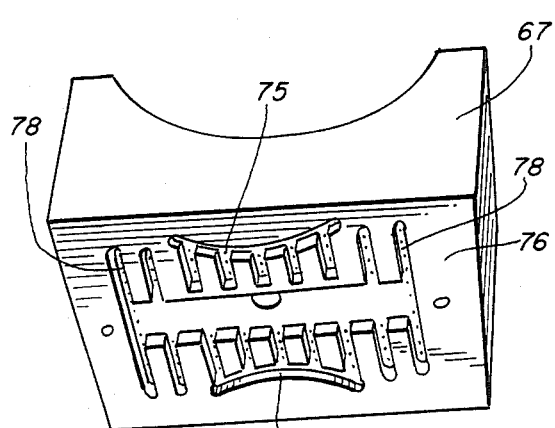
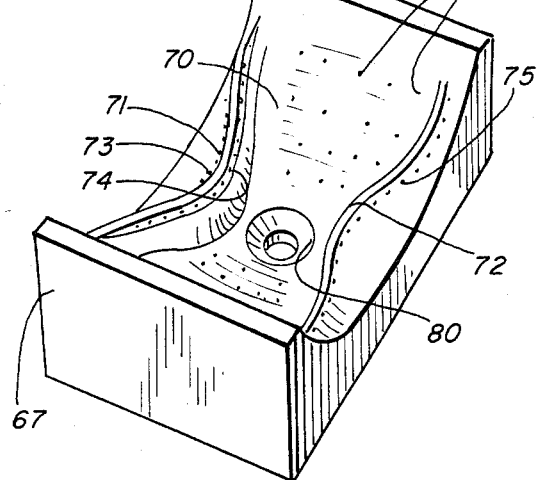

MACHINE AND METHOD FOR MANUFACTURING A DISPOSABLE ABSORBENT CONTINENCE PAD

TECHNICAL FIELD

This invention pertains to a machine and method for manufacturing a disposable absorbent continence pad. The continence pad has a shell formed of molded thermoplastic material with compound curved contours to conform to a wearer's body. The shell has a pocket for holding a fibrous absorbent material and the pocket is covered with facing material. The continence pad is formed by operations at a series of stations including a shell-forming station wherein special provisions are made for rapidly cooling the thermoplastic material from which the shell is formed, a slitting station wherein the facing material has specially-located slits formed therein to accommodate the lack of stretchability of the facing material in one direction, and a sealing station wherein the facing material is bonded to the shell with structure for precluding any tendency for wrinkles in the facing material.

BACKGROUND ART

It is generally known to mold articles from thermoplastic material and to heat seal a pair of members together.

DISCLOSURE OF THE INVENTION

A primary feature of the invention is to provide a new and improved machine having a series of work-performing stations for manufacturing a disposable absorbent continence pad having a molded shell of thermoplastic material to define a pocket for receiving a pad of fibrous absorbent material and with the product being completed by the sealing of facing material to the perimeter of the shell.

Another feature of the invention is to provide a method having a series of novel steps to manufacture the product, as defined in the preceding paragraph.

An object of the invention is to provide a machine for manufacturing a disposable absorbent continence pad comprising, means for advancing a web of thermoplastic material through a series of stations including a shell-forming station, means at said shell-forming station for molding a series of shells in said web of thermoplastic material, a sealing station, a slitting station in advance of the sealing station through which a length of facing material travels, means at the slitting station for making less than full-width cuts in the facing material which cuts will overlie said web of the thermoplastic material at locations between shells at said sealing station, and means at the sealing station for sealing said facing material to the perimeter of said shells.

Still another object of the invention is to provide a machine as defined in the preceding paragraph wherein said means at the shell-forming station comprises a lower vertically-movable frame having a series of concave molds, a vertically-movable box overlying said frame, means on said vertically-movable box for coaction with said molds to shape the perimeter of the shells, means for moving said frame and box to bring said box into sealing relation with said molds, means for drawing a vacuum through portions of said molds to assist in holding said thermoplastic material, a series of plugs movably mounted on said box overlying said molds, means for lowering said plugs into the molds to conform the thermoplastic material into the molds, passages in said box for delivery of air under pressure downwardly around said plugs to assist in conforming the plastic material and passages in said molds, box and plugs for chilled liquid to remove heat from said thermoplastic material to set the shape of the shells.

Still another object of the invention is to provide a machine as defined in the preceding paragraphs wherein said means at the sealing station comprises a vertically movable frame, a series of pocket members carried on said frame and each having a concave interior to receive a molded shell and a pair of spaced-apart ribs, a vertically movable seal head overlying said pocket members, a plurality of seal members depending from said seal head and having perimeters shaped to coact with the pocket members and said ribs to press the facing material against the perimeter of the formed shells, each of said seal members having an interior opening, a shaped-plug within said interior opening, means yieldably holding the shaped-plug in a position to gently press the facing material as the sealing head is lowered, a suction cup within the concave interior of each pocket member and movably associated therewith, means for lifting said suction cups relative to said frame to enable said suction cups to engage the undersides of said shells prior to upward movement of said frame, movable side plates on said sealing head for clamping against the pocket members to hold the facing material in position and seal the interior of the pocket members, and vacuum passages in said pocket member extending to the concave interior as well as to locations at both sides of said ribs.

An additional object of the invention is to provide a machine for manufacturing a disposable absorbent pad from thermoplastic material comprising, a shell-forming station, a lower vertically-movable frame at said station having a series of concave molds, a vertically-movable box overlying said frame, means on said vertically-movable box for coaction with said molds to shape the perimeter of the shells, means for moving said frame and box to bring said box into sealing relation with said molds, means for drawing a vacuum through portions of said molds where the middle parts of the shells are formed to assist in holding said thermoplastic material, a series of downwardly-extending plugs movably mounted on said box overlying said molds, means for lowering said plugs into the molds to conform the thermoplastic material to the molds, passages in said box for delivery of air under pressure downwardly around said plugs to assist in conforming the plastic material and passages in said molds, box and plugs for chilled liquid to remove heat from said thermoplastic material to set the shape of the shells.

A further object of the invention is to provide a machine for manufacturing a disposable absorbent continence pad having a formed shell with a pocket covered by facing material comprising, a slitting station, a plate at said slitting station on which said facing material rests, a frame overlying said plate, means for moving said frame toward and away from said plate, a stripper plate yieldably mounted on and below said frame for pressing said facing material against said plate, a pair of transversely reciprocable knife carriers on said frame having a plurality of depending knives, slots in said stripper plate and plate to permit said knives to pass through the facing material captured therebetween, and means for reciprocating said knife carriers to make less than full-width slits in said facing material.

An additional object of the invention is to provide a machine for manufacturing disposable absorbent continence pads having a molded shell and a cover of facing material and having means at a sealing station comprising, a vertically movable frame, a series of pocket members carried on said frame and each having a concave interior to receive a molded shell, a vertically movable seal head overlying said pocket members, a plurality of seal members depending from said seal head and having perimeters shaped to coact with the pocket members to press the facing material against the perimeter of the formed shells, each of said seal members having an interior opening, a shaped plug within said interior opening, means yieldably holding the shaped plug in a position to gently press the facing material as the sealing head is lowered, and movable side plates on said sealing head for clamping against the pocket members to hold the facing material in position and seal the interior of the pocket members.

A further object of the invention is to provide a method of making a disposable absorbent continence pad having a preformed shape for conformance with the body of a wearer including a shell with a curved bottom wall and side walls defining a pocket to hold a fibrous absorbent material and a fluid-transmitting facing material sealed to the perimeter of the shell to enclose the fibrous absorbent material in the shell comprising, advancing a length of thermoplastic foam material in a series of index steps through a plurality of successive stations, heating said foam material at a heating station, molding a plurality of said shells at a shell-forming station, inserting the fibrous absorbent material in said shells at a stuffing station, advancing a web of said facing material to a slitting station through which said shells pass without work being performed thereon, slitting said facing material at spaced locations along the length thereof at said slitting station to form a series of transverse slits, and sealing said facing material to said shells at a sealing station with the slits in the facing material disposed between successive shells to permit the facing material to adjust to the shape of the shell.

BRIEF DESCRIPTION OF THE DRAWINGS

FIG. 1 is a perspective view of the disposable, absorbent continence pad;

FIG. 2 is a transverse sectional view, taken generally along the line 2—2 in FIG. 1;

FIG. 3 is a diagrammatic plan view of the machine for manufacturing the continence pad;

FIG. 4 is a diagrammatic front elevational view of the machine shown in FIG. 3;

FIG. 5 is a front elevational view of the structure at a shell-forming station;

FIG. 6b is a sectional view, taken generally along the line 6b—6b in FIG. 6a;

FIG. 7 is a fragmentary perspective view, showing two rows of formed shells of the continence pad and the conveying structure therefor;

FIG. 8 comprises perspective view of a coacting seal head and pocket member;

FIG. 9 is a perspective view of the underside of a pocket member;

BEST MODE FOR CARRYING OUT THE INVENTION

Figure 13:
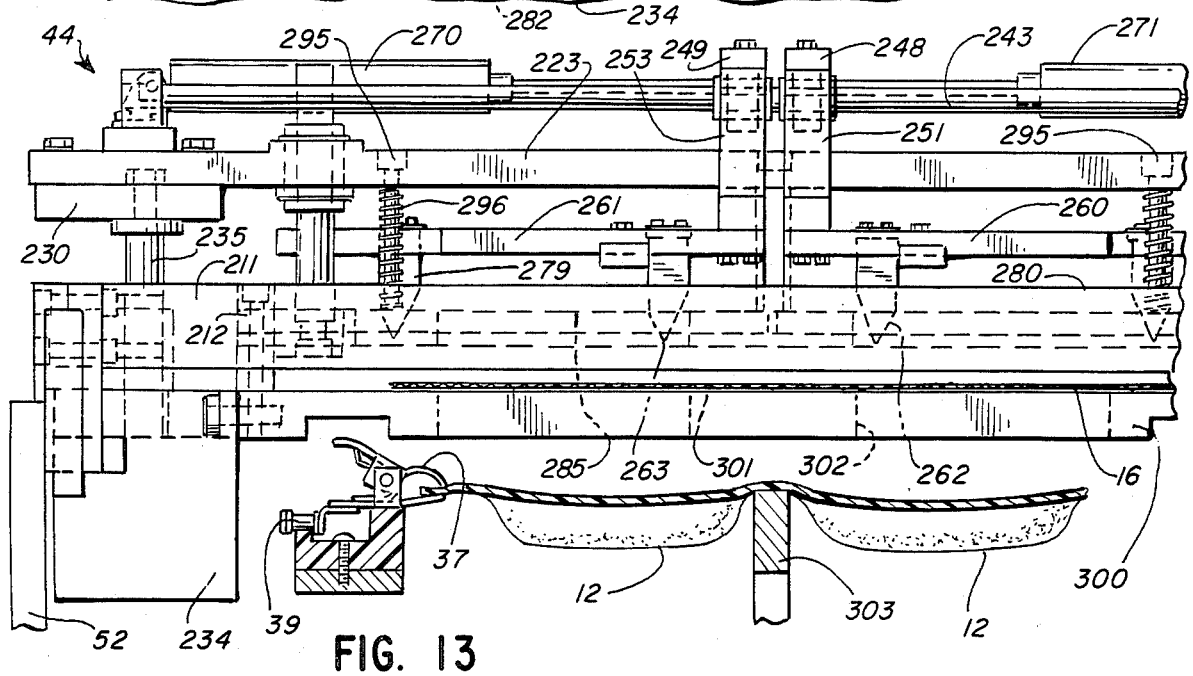
FIG. 13 is a fragmentary side elevational view of the structure at the slitting station, looking toward the right-hand side of FIG. 12.

The disposable absorbent continence pad is shown in FIGS. 1 and 2, with the product in an intermediate step of manufacturing shown in FIGS. 7 and 13.

The continence pad is shaped for comfortable fitting to the body of a wearer and has a flexible structural shell, formed of soft, thermoplastic material. The thermoplastic material is a closed cell plastic foam. The continence pad is indicated generally at 10, in FIGS. 1 and 2. The shell 12 is formed with an interior pocket to receive a filler 14 which is a pad of fibrous absorbent material, which is retained within the shell by a cover 16 of a porous facing material which is sealed at its perimeter to the perimeter of the shell 12. This facing material may be formed of composite layers, with one layer being a polyethylene material and the other side being Mylar, and which can be heat sealed to the shell.

The shell 12 has a bottom wall 18 with a transverse curvature, as seen in FIG. 2, and a longitudinal curvature, as seen in FIG. 7. The bottom wall 18 merges with a pair of side walls 19 and 20 having compound curves intermediate the length of the shell, as seen in FIG. 2, and which have a pair of flanges 21 and 22, respectively, at their upper ends which extend completely around the upper perimeter of the shell. The side walls along with an upward curvature of a pair of end walls, one of which is shown at 24, which merge with the side walls 19 and 20 and the bottom wall 18 define the pocket. In plan view, the continence pad 10 has its narrowest dimension along a line generally coincident with the section line 2—2 in FIG. 1 and which curvingly enlarges to the portions defined by the end walls and with the flange continuations associated with the end walls having a curved periphery.

The machine and method for making the continence pad 10 is shown generally in FIGS. 3 and 4.

Rolls 30 and 31 of the thermoplastic material for forming the shell are located at one end of the machine, with the web being led from one or the other of the rolls through a series of stations. The web of material is fed flat to the machine by means of the conveying structure shown in FIG. 7. In this view, the web 34 is shown formed into the shells 12, rather than being flat as it initially enters the first station of the machine. The web 34 has opposite edges 35 and 36 which are engaged by respective series of releasable grippers 37 and 38. As conventionally known, the series of grippers 37 and 38 are each associated with an endless chain 39. The endless chains are movable mounted on the frame and power driven to move the series of grippers 37 and 38 longitudinally through a number of processing stations of the machine.

Referring to FIGS. 3 and 4, the processing stations include a heating station, indicated generally at 40, which heats the web 34 of plastic material prior to entering a shell-forming station, indicated generally at 41. At the shell-forming station 41, the web 34 is formed into the shape shown in FIG. 7 by structure more particularly described hereinafter.

Figure 10:
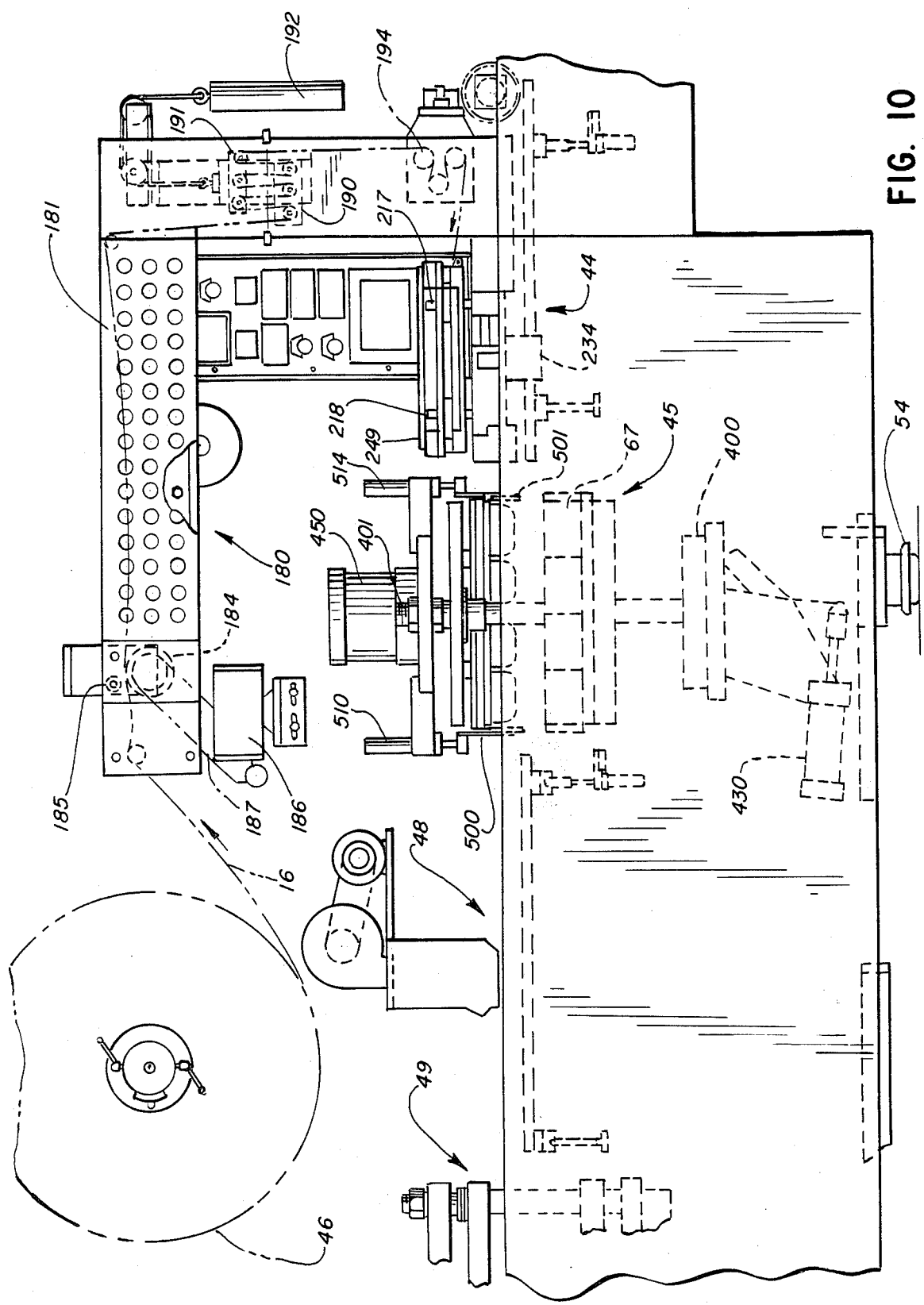
FIG. 10 is a fragmentary front elevational view of the machine showing a control station and a slitting station and subsequent stations.

The next processing station is a stuffing station 42 wherein a pad of the fibrous absorbent material 14 is positioned within the pocket defined within the shell 12. Succeeding stations are shown particularly in FIG. 10 and include a slitting station 44 and a sealing station 45. The slitting station 44 places a predetermined pattern of slits in a web of facing material 16 coming off a supply roll 46 and the sealing station 45 seals the facing material 16 to the flanges 21 and 22 of the shell. A cooling station 48 cools the completed product and with the product being made in multiples, the product is separated into individual products at a cutting station 49. Additional stations are a scrap removal station 50 and an exit conveying station 51.

The machine has a structural framework rigidly interconnecting the structure at the various stations, with frame sections 52 and 53 having front and rear plates and being connected by an intermediate frame section 54 and with the frame sections 52 and 53 having a plurality of adjustable floor-engaging supports 54.

The continence pads are formed in multiples and separated at the previously-described cutting station 49. The particular machine illustrated utilizes a web 34 of thermoplastic material of sufficient width to form two shells 12 transversely thereof as seen in FIG. 7. The structure at the shell-forming station 41, the stuffing station 42 and the sealing station 45 is in multiples to simultaneously operate on four of the shells 12 lengthwise of the web in each of the two transverse rows for a total of eight shells in each sequential advance of the web 34 and with a dwell of the web at each of the stations.

Figure 6:
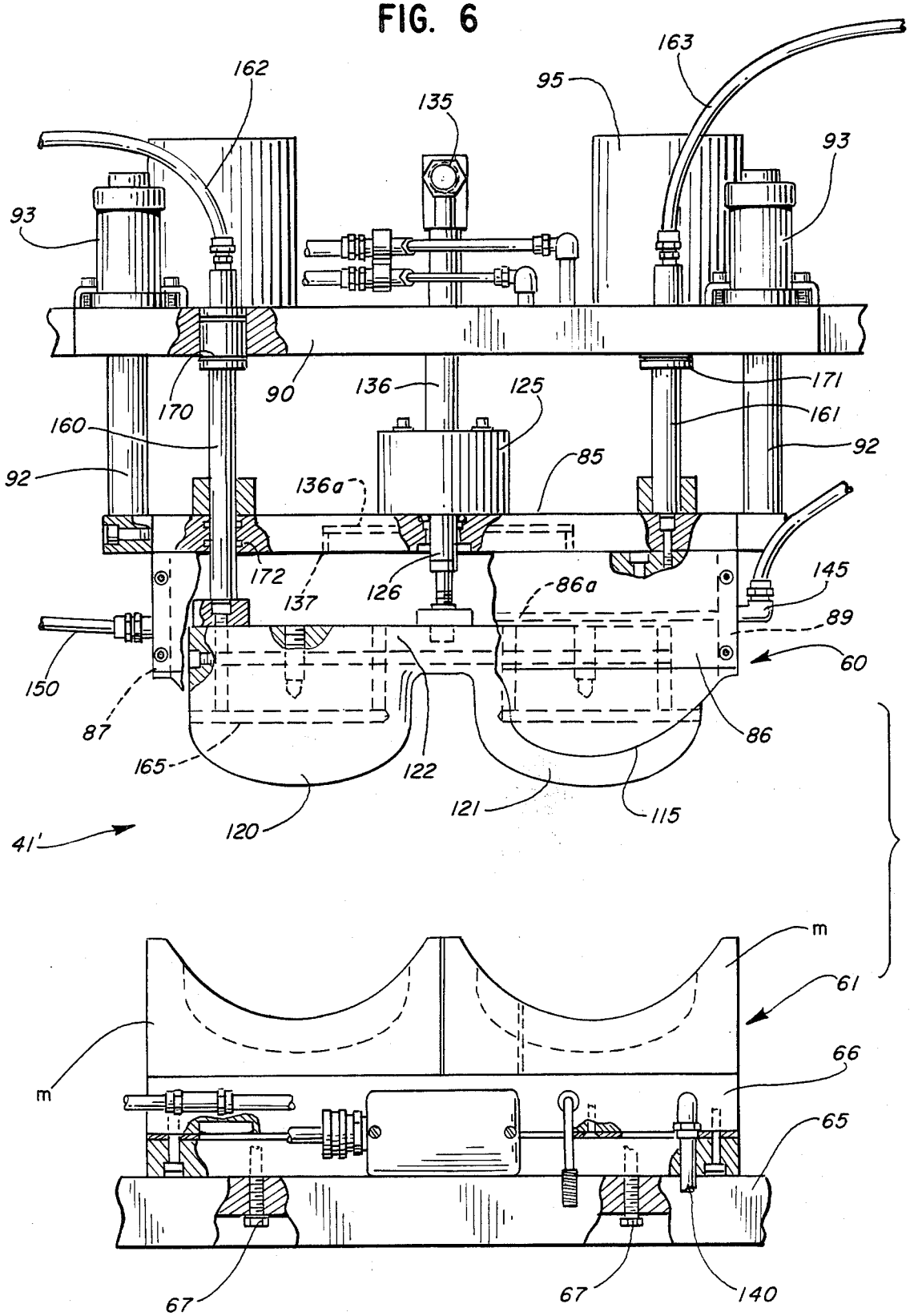
FIG. 6 is a side elevational view of the structure shown in FIG. 5, looking toward the left-hand side thereof and with parts broken away.

The shell-forming station 41 is shown particularly in FIGS. 5 and 6 and has a box, indicated generally at 60, movably mounted on the machine frame and located above a mold, indicated generally at 61, which is movably-mounted on the frame. The structure for moving the mold 61 up and down is of the same construction as that associated with a lower member to be described at the sealing station 45 and reference may be made thereto. The view of FIG. 5 is looking toward the front of the machine and with the web 34 travelling from right to left.

The mold 61 has a base member 65 having a manifold block 66 secured to the upper side thereof by fasteners 66a. The manifold block 66 mounts a plurality of mold members M, with there being eight of these mold members in the particular machine disclosed herein. The mold members M are generally of the construction shown in FIG. 9 and the lower part of FIG. 8. These Figures acutally show a pocket member 67 as used at the sealing station. The mold members M are of the same construction as the pocket members 67 except for the omission of a suction cup opening and, therefore, a description of the pocket members provides the necessary description for the mold members.

The pocket member is in the form of a block having a concave interior 70, with the same contour as the shell 12 of the continence pad. A pair of raised curved ribs 71 and 72 extend along the sides of the pocket member. Associated with each of the ribs 71 and 72, and extending along both sides thereof, are a series of small diameter through passages, with the series of passages 73 and 74 being shown in association with the rib 71 and one of the series of passages associated with the rib 72 shown at 75. These passages extend through the pocket member 67 to the bottom face 76 thereof. Additionally, there are several rows of even smaller diameter passages extending through the pocket member 67 from the concave central portion thereof to the underside, with these passages being identified at 78. All of the passages in the pocket member 67 permit the upper side thereof to either be exposed to atmosphere or to a vacuum source. In order to avoid roughening the surface of the thermoplastic material, the passages 78 are quite small in diameter, so that application of a vacuum therethrough will not deform the surface of the hot thermoplastic material. The pocket member 67 is shown as having a central suction cup opening 80 which is shaped to permit mounting of a suction cup. This suction cup opening is omitted when the pocket member 67 is used as a mold M at the shell-forming station 41.

The box 60 has a top plate 85 to which are secured in depending relation a pair of opposed end walls 86 and 88 (FIGS. 5, 6 and 6a) and a pair of side walls 87 and 89. The end walls 86 and 88 define with the side walls 87 and 89 a generally rectangular box structure which, with the top plate 85, are movably supported beneath a support plate 90 rigidly secured to the frame of the machine.

The box 60 is movably guided for up and down movement relative to the support plate 90 by guide rods 92 at the four corners thereof which, at their lower ends, are secured to the top plate 85 and which are movable within linear bearings 93 secured to the support plate 90 and extending upwardly therefrom. Up and down movement of the box 60 relative to the support plate 90 is by operation of four fluid cylinders 95 fixed to the upper side of the support plate 90 and each having a cylinder rod 96 which extends through the support plate 90 and is secured to the top plate 85 of the box. The box 60 is shown in a lowered position relative to the support plate 90 in FIGS. 5 and 6, as a result of the cylinder rods being extended.

Figure 6A:
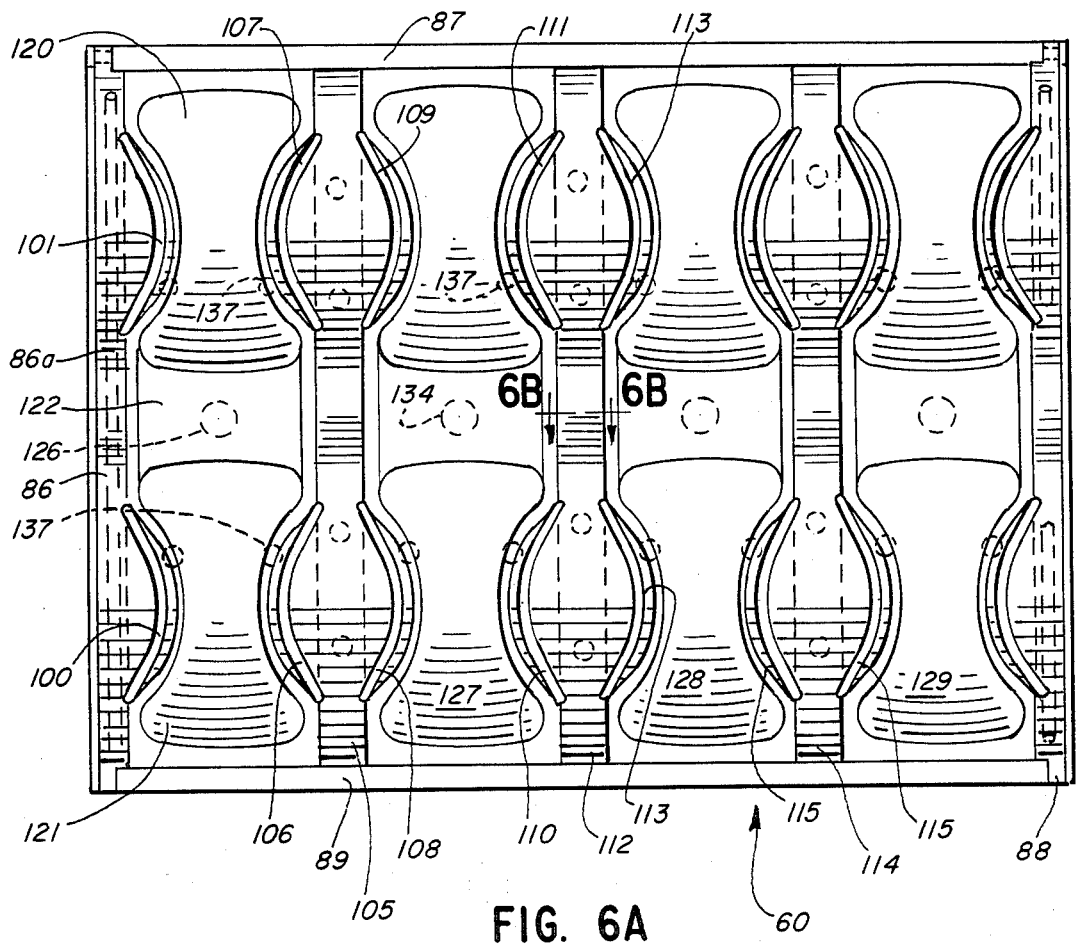
FIG. 6a is a fragmentary bottom plan view of the box at a shell-forming station.
Figure 6B:
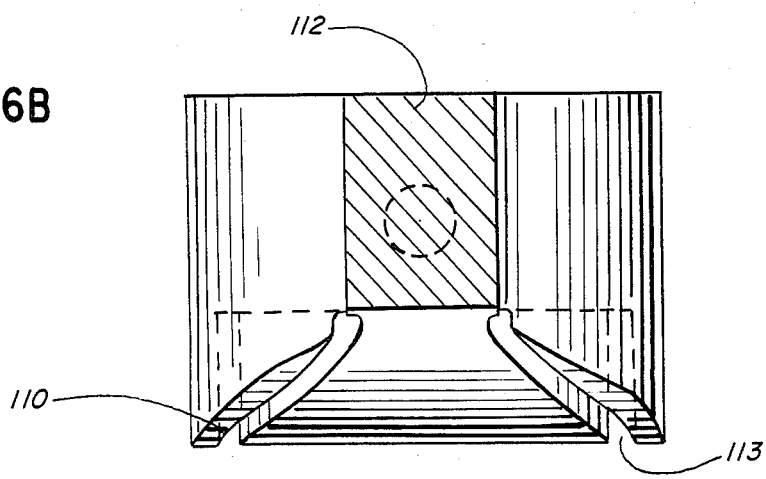

A bottom plan view of the box 60 is shown in FIG. 6A wherein the end plate 86 has a pair of inwardly-curved, concave grooves 100, 101 which coact with the rib 71 of a mold M.

A series of spaced inner members extend between the side walls 87 and 89. One of these inner members 105 has a pair of inwardly-curved, concave grooves 106 and 107, each of which can coact with the rib 72 of a pair of mold members M. A pair of additional, inwardly-curved concave grooves 108 and 109 on the member 105 are associated with a second pair of the mold members M and with a pair of inwardly-curved concave grooves 110 and 111 on an adjacent inner member 112 coacting with a pair of mold members M to form a second pair of shells 12. There are additional grooves 113 and a third similar inner member which coacts with end wall 88 and has grooves 115.

With the mold 61 elevated from the position shown in FIGS. 5 and 6 into a contacting position with the underside of the side walls 87 and 89 and the end walls 86 and 88 having a curved edge 115, there is an effective seal for drawing a vacuum, as to be described.

To facilitate formation of the shells 12, there is a plurality of movable plugs associated with the box 60, with there being a pair of plugs 120 and 121 integral with a member 122. Each pair of plugs has movement independently of the box 60. As seen in FIG. 6, a pair of plugs 120 and 121 is movable relative to the box 60 by means of a fluid cylinder 125 having a rod 126 connected at its lower end to the member 122. A passage through the top plate 85 for the rod 126 is sealed by an O-ring. These plugs each have a convex shape, generally similar to the form of the molded shell 12 whereby the plugs can be lowered relative to the box to depress the hot thermoplastic material of the web 34 into the mold members M. A plug of each additional pair is identified at 127, 128 and 129.

The cycle of operation at the forming station 41 is to first raise the mold head 61 upwardly to be immediately beneath the plane of the flat web 34, followed by lowering the box 60 to clamp the web against the mold members M. The pairs of plugs, for example, plugs 120 and 121 are then lowered to move the hot thermoplastic material downwardly into the mold members M. Air under pressure is directed downwardly against the thermoplastic material to assist in shaping the material. This air is delivered through a line 135 to a pipe 136 connected to passages 136a in the top plate with openings 137 to the interior of the box 60. This air can flow downwardly around the plugs and against the thermoplastic material. A vacuum is then applied to the mold member cavities to firmly seat the thermoplastic material. Additional fluid cylinders 130-132 operate the other pairs of plugs, with the cylinder 130 having the rod 134 shown in FIG. 6a.

An important feature of the invention is the rapid cooling of the thermoplastic web 34 after forming the shells 12. The thermoplastic material, being a foam material, has a considerable amount of air in it. If the formed shells were advanced out of the forming station before cooling of the thermoplastic material, it would be possible for the plastic to shrink as final cooling occurs, with resultant reduction in the dimensions of the shell.

The manifold block 66 is formed with internal passages 138 for receiving a continuous flow of chilled liquid from a line 140 for cooling of the mold members M. A series of drilled air passages 142 and 143 in the manifold block 66 communicate with a passage 144 connected by a tube to a four-way valve whereby the passages 78 in the mold member M can either be connected to atmosphere or to a vacuum source, depending upon the position of the four-way valve.

Of considerable importance is the cooling of the box 70 and the forming plugs, of which plugs 120 and 121 are typical. Each of the end walls 86 and 88, as well as the intermediate members 105, 112 and 114 are provided with drilled passages, such as passage 86a in end wall 86, whereby chilled liquid can flow therethrough, with these respective members having fittings at opposite ends to which tubing is connected. The connections are shown at 145 and 146 for the end walls 86 and 88 and with the fittings for the intermediate walls being at 147, 148 and 149 and being connected to the side wall 87, with openings therethrough communicating with ends of the drilled passages in the intermediate members. The opposite side wall 89 has similar connections for receiving the liquid leaving the drilled passages in the intermediate walls and also there are outlet flow connections at opposite ends of the end walls 86 and 88, such as hose 150.

All of the plugs are also provided with drilled water passages 165.

As seen in FIG. 6, there are a pair of tubular water posts 160 and 161 which have flexible liquid tubes 162 and 163 connected to their upper ends and which, at their lower ends, connect to the water passages 165 whereby there can be flow from tube 162 through the water post 160 through the drilled passage 165, with outflow through the water post 161 and the tube 163. Each of these water posts 160 and 161 is movably mounted with respect to the support plate 90 by linear ball bushings 170 and 171 and a pair of O-rings 172 slidably seal the water posts relative to the top plate 85 of the box 60. Each pair of plugs has a pair of the water posts, with the water posts 175 and 176 and associated tubes 177 and 178 being seen in FIG. 5.

With the separate circuits for liquid in the mold head 61, the box 60 and the plugs, it is possible to have different temperature liquid in the various circuits, dependent upon the requirements for enabling good forming as well as quick chilling of the plastic. One or more of the circuits can have a liquid including antifreeze, whereby the actual temperature of the liquid can be below 32° F.

After forming of the shells 12 and chilling of the plastic, the plugs and box 60 are raised and the mold 61 is lowered, with conveyance of the eight formed shells 12 to the stuffing station 42 wherein the eight shells can either be manually or automatically stuffed with the fibrous absorbent material filler and the filled shells are then advanced to a slitting station 44. At the slitting station 44, the shells 12 and the filler material contained therein are merely passive and the facing material 16 is spaced above the filled shells and slits are cut.

A control station, indicated generally at 180, overlies the slitting station 44 and the sealing station 45 and has a control panel 181 for controlling the conveying system and the mechanism at the various stations of the machine.

The facing material 16 is drawn off the supply roll 46 by a feed couple including a driven roller 184 and an idler roller 185. The driven roller 184 is driven from a frame-supported motor 186 by a drive belt 187. The web 16 of facing material travels through a festoon structure 190 having a series of lower fixed rollers and a series of upper movable rollers 191. The upper movable rollers 191 are pulled upwardly by a weight 192 whereby a quantity of the web is stored within the festoon structure 190 and drawn therefrom at a controlled rate by a nest of rollers 194 suitably driven as by a chain drive with a sprocket take off from the chains 39 which mount the web clips 37 and 38. The web 16 travels through the slitting station 44 and through the sealing station 45 wherein it is caused to advance along with the formed shells 12 of the continence pads by a pair of endless idler belts (not shown) overlying the conveyor clips 37 and 38 and which exert sufficient pressure on the web against the conveyor clips to cause it to move with the conveyor clips.

The facing material is preferably of a spun polyethylene which has stretch in only one direction. In applying this facing material to the shells 12 at the sealing station 45, the material can stretch transversely, but cannot stretch in a longitudinal direction. The heat sealing of the facing material to the irregular contour of the shells can result in wrinkles at the heat seal perimeter where the facing material is joined to the shell, unless provision is made for stretch of the facing material in the longitudinal direction. The slitting station 44 has structure to provide slits in the facing material in parts thereof which will lie between successive pairs of shells 12 in order to enable the facing material that is being heat sealed to a shell to adjust and be heat sealed to the perimeter of the shell without wrinkles.

Figure 14:
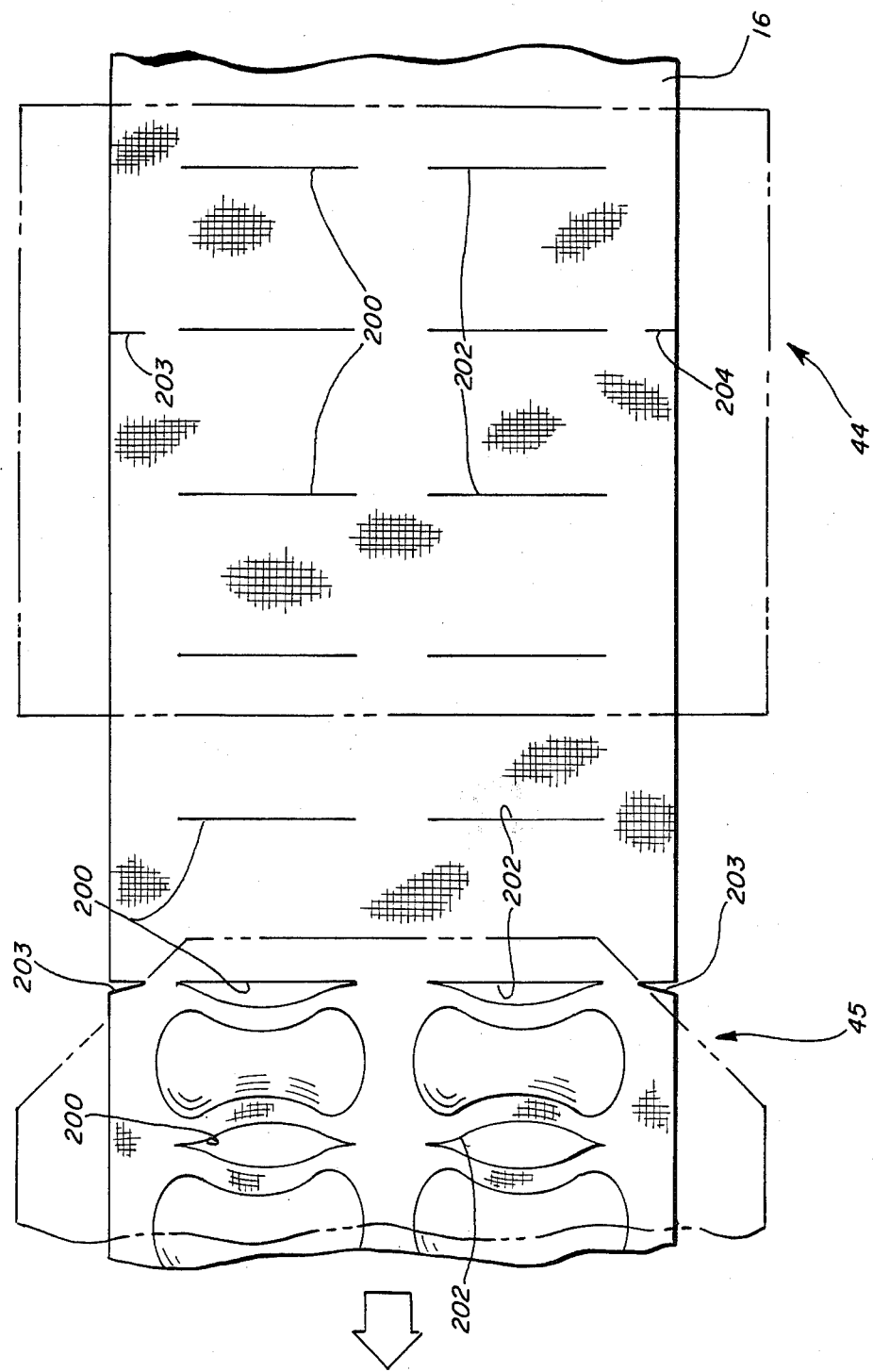
FIG. 14 is a diagrammatic view, showing in plan the facing material and the operations performed thereon at the slitting station and the sealing station.

These operations are shown diagrammatically in FIG. 14 wherein the web 16 is shown with the slits that have been cut at the slitting station 44 and the opening of the slits which occurs at the time of sealing in the sealing station 45. A first row of slits 200 is formed in the web 16 to extend partially between the centerline of the web and the edge and are spaced apart to have each slit overlie a space between two of the formed shells which are located beneath and at a distance from the web 16 in the slitting station 44, as seen in FIG. 13. A second, similar series of slits 202 is formed in the web intermediate the centerline and the edge thereof and are similarly spaced longitudinally of the web.

Additionally, a single pair of edge slits 203 and 204 are formed in the web in each cycle of operation at the slitting station 44, to provide some give in the facing material at the edge thereof at the sealing station and as seen in FIG. 14.

Figure 11:
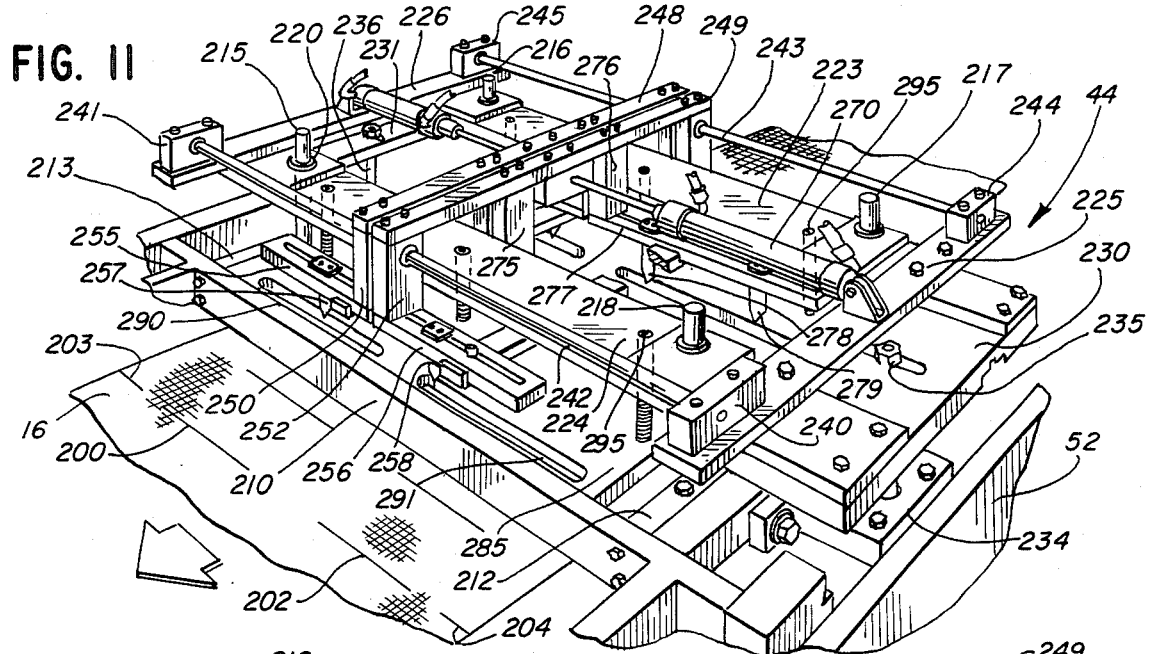
FIG. 11 is a perspective view of the mechanism at the slitting station.
Figure 12:
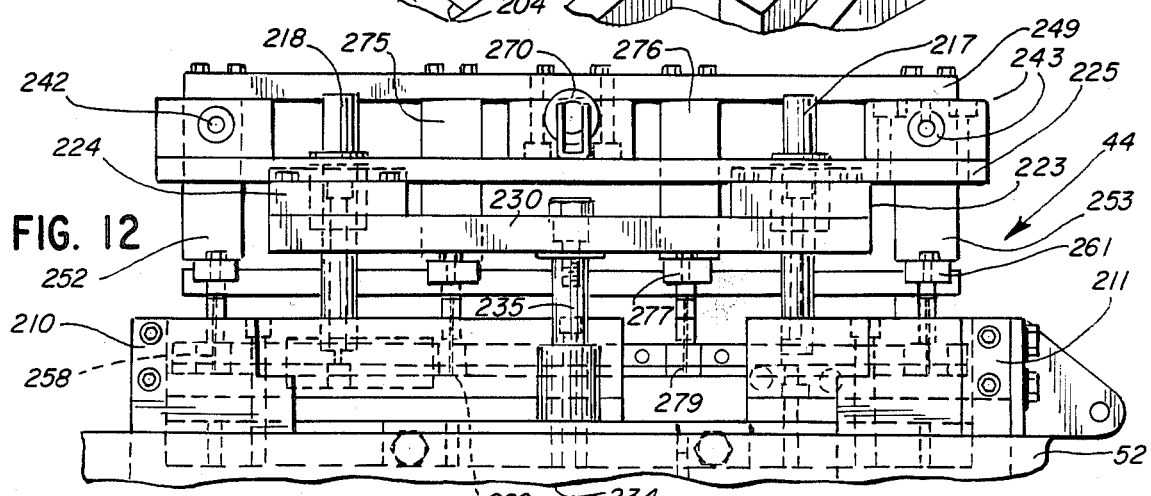
FIG. 12 is a front elevational view of the mechanism shown in FIG. 11.

The structure at the slitting station 44 is shown particularly in FIGS. 11–13. The machine frame supports a fixed base structure including a pair of transverse members 210 and 211 and a pair of spaced longitudinal members 212 and 213 which, at their ends, are connected to the transverse members 210 and 211. Fixed to, and upstanding from, these longitudinal members 212 and 213 are four guide rods 215–218 which movably guide a slitting head for up and down movement by means of linear bearings, such as the linear bearing 220 supported in the slitting frame. The slitting head has a pair of transverse plates 223 and 224 interconnected at their ends by a pair of longitudinally-extending tie bars 225 and 226, with the transverse members 223 and 224 housing the linear bearings 220 for the guide rods 215–218.

The opposite ends of the transverse plates 223 and 224 are interconnected by the respective tie bars 230 and 231, with each of these tie bars being connected to a rod of a cylinder for causing up and down movement of the slitting frame. A cylinder 234 has a rod 235 connected to the tie bar 230 and a second cylinder at the rear of the machine (not shown) has a rod 236 connected to the tie bar 231.

Each of the tie bars 225 and 226 mounts a pair of mounting blocks, with opposed mounting blocks 240 and 241 on the tie bars having a guide rod 242 extended there-between. A second guide rod 243 is extended between a pair of mounting blocks 244 and 245.

A pair of knife carriers in the form of longitudinally-extending tie bars 248 and 249 each have, at their opposite ends, a pair of depending mounting blocks which carry linear bearings to enable movement of the mounting blocks along the length of the guide rods. The tie bar 248 has the mounting blocks 250 and 251 and the tie bar 249 has the mounting blocks 252 and 253. The underside of each of these mounting blocks has a knife holder affixed thereto and extending, respectively, toward the front and rear of the machine. Mounting block 250 has the knife holder 255 and the mounting block 252 has the knife holder 256, with each knife holder having a longitudinal slot for each holding a respective adjustable depending knife 257 and 258. The mounting blocks 251 and 253 carry similar knife holders 260 and 261, with each having a depending knife 262 and 263. The knives 257 and 258 cut the leading pair of slits, shown in FIG. 14, at the slitting station, while the knives 262 and 263 cut the trailing pair of slits shown in FIG. 14. The slitting action is caused by operation of the cylinders, including cylinder 234, to lower the slitting head and to lower the knives down across the plane of the web 16 of the facing material. The knives are then caused to move outwardly by operation of a pair of cylinders 270 and 271 pivotally connected at one end to the respective tie bars 225 and 226 and which have their rods extended to connect with a pair of blocks fixed to the underside of the longitudinally-extending tie bars 248 and 249.

There are four additional mounting blocks depending from the tie bars 248 and 249 which each additionally carry a knife holder similar to knife holders 255 and 256 previously described. The pair of depending mounting blocks associated with the tie bar 249 are shown at 275 and 276. The mounting block 276 has a knife holder 277 which is considerably longer than the knife holder 256 to mount a pair of knives 278 and 279. The knive 279 cuts the edge slit 204 and the knife 280 associated with the tie bar 248 cuts the edge slit 203. A knife associated with the mounting block 275 is seen in FIG. 12 at 282.

The slitting head additionally carries a stripper plate 285 provided with elongate slots, such as the elongate slots 290 and 291 for the knives 257 and 258, which enable downward movement of the knives through the stripper plate to pierce the web 16 followed by movement of the knives away from each other by operation of the cylinders 270 and 271 to cut the slits in the web.

The stripper plate 285 is floatingly mounted to the stripper frame, with a limit to its downward movement relative thereto by means of headed bolts 295 which are movable in the plates 223 and 224 and have their lower ends fixed to the stripper plate 285 and which are each surrounded by a compression spring 296. The bolts 295 limit the maximum distance between the plates 223 and 224 and the stripper plate 285. As the stripper frame descends, the stripper plate 285 will engage the upper surface of the web 16, with the latter being supported by a fixed base plate 300. Further descent of the slitting head will lower the knives an additional distance to pierce the web 16 for cutting of the slits. Upon lifting of the slitting head, the knives will first retract, with the stripper plate remaining against the web to assure that the knives are separated from the web and, thereafter, the stripper plate will move upwardly away from the web. Base plate 300 has slots therethrough of an adequate length to permit the cutting travel of the knives, with a pair of the slits being seen at 301 and 302 in FIG. 13.

The web 34 is supported intermediate the shells by an elongate support bar 303.

A succeeding index of the web of facing material and the formed shells brings the two together in the sealing station 45 and in the general relation shown in FIG. 14 wherein the slits are interposed between shells.

Figure 15:
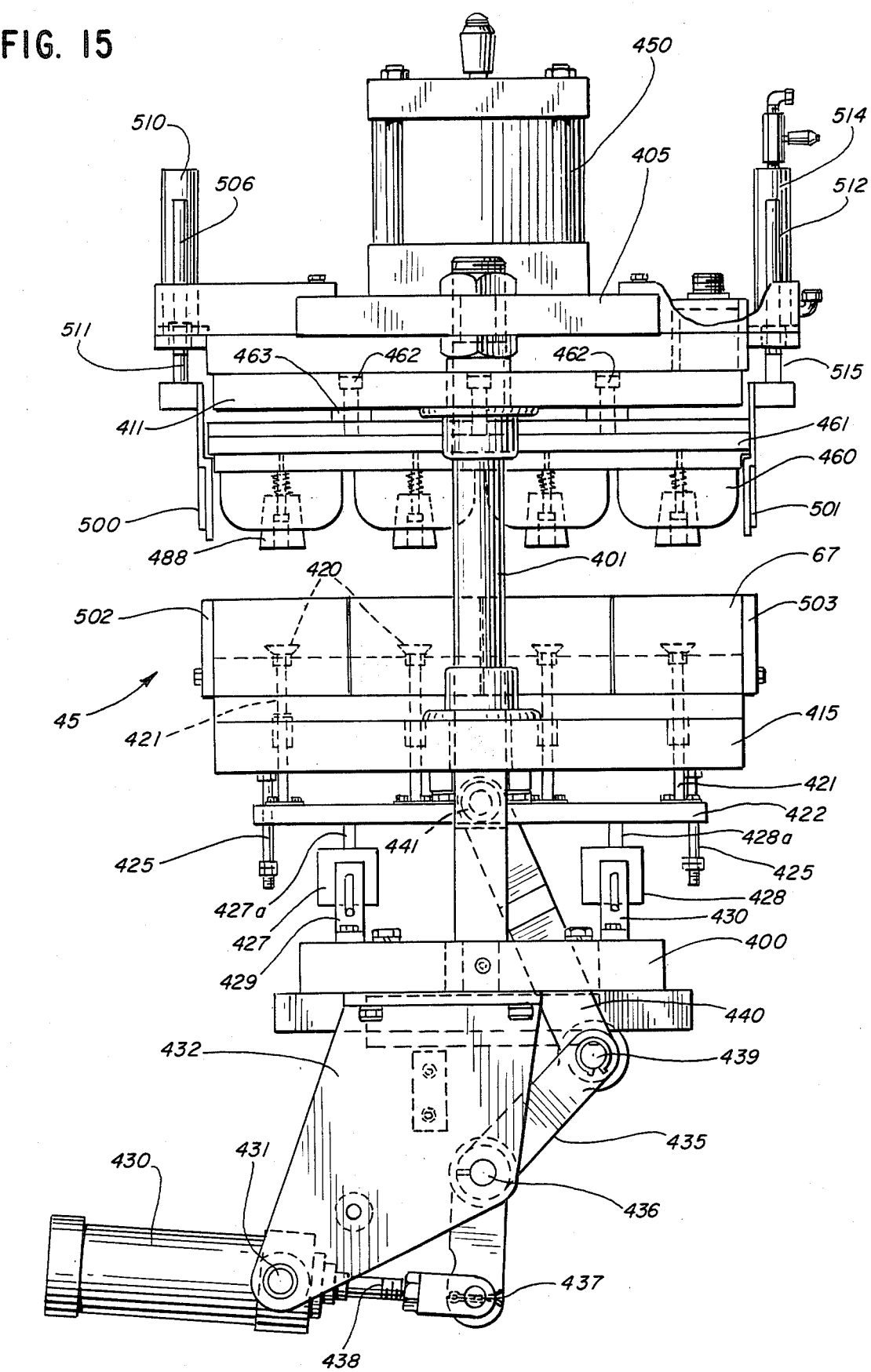
FIG. 15 is a front elevational view of the mechanism at the sealing station.
Figure 16:
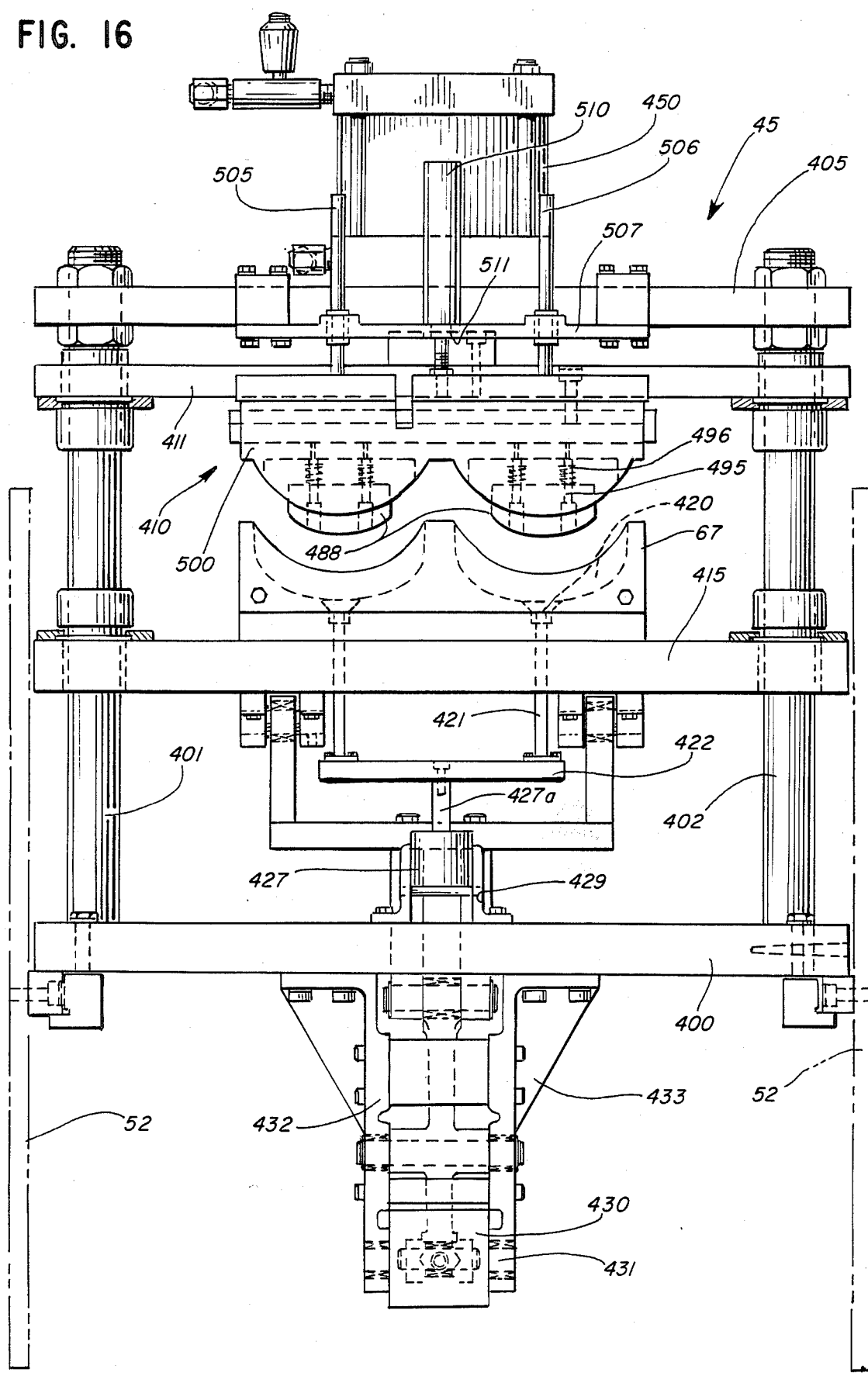
FIG. 16 is a side elevational view of the structure shown in FIG. 15 and looking toward the left-hand side thereof.

The structure at the sealing station 45 is shown particularly in FIGS. 15 and 16.

The machine frame plates 52 support a base plate 400 which mounts a pair of upstanding guide posts 401 and 402 at the front and rear of the machine, respectively, which are interconnected at their upper ends by a top support plate 405.

A seal head, indicated generally at 410 has a plate 411 movably mounted on the guide posts 401 and 402. A plate 415 beneath the seal head 410 mounts the previously-described pocket members and is movably guided on the guide posts 401 and 402. Each of the pocket members 67 has a suction cup 420 associated therewith which is mounted at the upper end of a rigid tube 421 extending through the central suction cup opening 80 in the bottom of each of the pocket members 67. These tubes 421 are fixed to a vacuum manifold plate 422 which is movable independently of the support plate 415. The vacuum manifold plate 422 is guided for vertical movement along a plurality of stop shafts 425 depending from the underside of the plate 415. The suction cups 420 move relative to the pocket members 67 between the retracted position seated in the central opening 80 and the extended position shown in FIG. 15. The suction cups and the vacuum manifold plate 422 are moved relative to the plate 415 by a pair of fluid cylinders 427 and 428 having rods 427a and 428a and which are mounted to the upper side of the base plate 400 by brackets 429 and 430.

A fluid cylinder 430 pivotally mounted at 431 to a pair of brackets 432 and 433 depending from the underside of the base plate 400 moves the plate 415 up and down on the guide posts 401 and 402 to raise and lower the pocket members 67. A bell crank 435 is pivoted at 435 between the brackets 432 and 433 and, at one end, is pivoted at 437 to the cylinder rod 438 and, at its other end, is pivoted at 439 to a link 440 which is pivotally connected at 441 to the underside of the plate 415. Extension of the cylinder rod 438 brings a leg of the bell crank and the link 440 into alignment when the plate 415 and the pocket members 67 are in the position shown in FIG. 16. The base plate 400 has a suitable interior opening to permit movement of the link 440.

The plate 411 of the seal head 410 is movable up and down by operation of a fluid cylinder 450 secured to the upper side of the top support plate 405 and having a depending rod secured to the plate 411.

A plurality of seal members 460 depend from a heater plate 461 secured to the underside of the plate 411 by machine screws 462 and spaced therefrom by washers 463. A seal member 460 is shown particularly in FIG. 8 and has a wall 490 with a shaped depending perimeter 465 for coaction with a pocket member 67 to heat seal the facing material to the shell 12 at the flanges 21 and 22 of the shell, with there being sealing about the complete perimeter of the shell. The sides of the seal member are provided with the respective concave grooves 480 and 481 which receive the respective ribs 71 and 72 of the pocket member 67 therebetween to form a pair of generally parallel spaced-apart seals between the facing material and shell along the sides.

Each of the seal members 460 has a pair of openings 485 to movably mount a spring-loaded plug 488. The plug 488 is of a size to fit within the interior opening defined by the wall 490 and is movably mounted by a pair of headed pins 495 extended through the openings 485. A spring 496 surrounds each of the pins and urges the plug downwardly and outwardly of the seal member 460, but with the heads of the pins limiting this downward movement. In response to light pressure exerted against the plugs, they can move upwardly into the seal member 460 against the force of the springs 496.

The seal head 410 also mounts a pair of side plates 500 and 501 which can be lowered against the side mounting plates 502 and 503 for the pocket members 67 to make a seal in order that a vacuum may be established within the pocket members. The side plate 500 has a pair of guide rods 505 and 506 movably guided in a bracket 507 fixed to the top support plate 405. A fluid cylinder 510 fixed to the top support plate 405 has a rod 511 connected to the side plate 500.

The side plate 501 has a similar construction including guide rods, one of which is shown at 512 and a cylinder 514 having a rod 515 connected to the side plate.

The cylinders at the sealing station are cycled to perform the following sequence of operation:

The cylinders 427 and 428 are energized to lift the vacuum manifold plate 422 and the suction cups 420 to the raised position relative to the pocket members 67 as shown in FIG. 15. A vacuum is applied to the suction cups through the vacuum manifold plate 422 to have the suction cups engage and hold the underside of the shells 12.

The plate 415 is then raised by operation of the cylinder 430 to raise the pocket members 67 to the position shown in FIG. 16 which causes relative retraction of the suction cups 420 to have the shells fully seated in the pocket members. A vacuum is then applied through all of the described passages in the pocket members 67 to firmly draw the entire underside of the shell 12 into closely-confirming relation with the shape of the pocket members 67. The cylinders 510 and 514 are operated to lower the respective side plates 500 and 501 into sealing and clamped relation with the frame of the pocket member structure to assure good vacuum. The sealing head 410 is then lowered to initially bring the yieldable plugs 488 into contact with the upper surface of the facing material to eliminate wrinkles as facilitated by the elevated temperature of the plugs because of their being associated with the seal members 460 and the heater plate 461. The final downward movement of the seal head 410 brings the seal members 460 into firm contact with the pocket members 67 and, at the elevated temperature, a seal is made between the facing material and the shell to form a completed continence pad shown in FIGS. 1 and 2.

Thereafter, the completed products are advanced to the cooling station 48 and then the cutting station 49 wherein each individual continence pad is separated from the others for conveying away for subsequent packaging.

From the foregoing description of the structure at the various stations, it is believed that the various method steps involved in forming the product have been adequately described in connection with the sequence of operation of the structure.

We claim:

1. A machine for manufacturing a disposable absorbent continence pad comprising, means for advancing a web of thermoplastic material through a series of stations, including a shell-forming station, means at said shell-forming station for molding a series of shells with compound curved side walls in said web of thermoplastic material, a sealing station, a slitting station in advance of the sealing station through which a length of facing material travels, means at the slitting station for making less than full-width transverse cuts in the facing material spaced apart lengthwise of the facing material to overlie said web of thermoplastic material at locations between shells at said sealing station, and means at the sealing station for sealing said facing material to the perimeter of said shells.

2. A machine as defined in claim 1 wherein said means at the shell-forming station comprises a lower vertically-movable frame having a series of concave molds, a vertically-movable box overlying said frame, means on said vertically-movable box for coaction with said molds to shape the perimeter of the shells, means for moving said frame and box to bring said box into sealing relation with said molds, means for drawing a vacuum through portions of said molds to assist in holding said thermoplastic material, a series of plugs movably mounted on said box overlying said molds, means for lowering said plugs into the molds to conform the thermoplastic material into the molds, and passages in said box for delivery of air under pressure downwardly around said plugs to assist in confirming the plastic material, and separate and distinct passages in each of said molds, box and plugs for chilled liquid which can be at different temperatures in each of said passages to remove heat from said thermoplastic material to set the shape of the shells.

3. A machine for manufacturing a disposable absorbent continence pad comprising, means for advancing a web of thermoplastic material through a series of stations, including a shell-forming station, means at said shell-forming station for molding a series of shells in said web of thermoplastic material, a sealing station, a slitting station in advance of the sealing station through which a length of facing material travels, means at the slitting station for making less than full-width cuts in the facing material which cuts will overlie said web of thermoplastic material at locations between shells at a said sealing station, means at the sealing station for sealing said facing material to the perimeter of said shells, a vertically movable frame, a series of pocket members carried on said frame and each having a concave interior to receive a molded shell and a pair of spaced-apart ribs, a vertically movable seal head overlying said pocket members, a plurality of seal members depending from said seal head and having perimeters shaped to coact with the pocket members and said ribs to press the facing material against the perimeter of the formed shells, each of said seal members having an interior opening, a shaped-plug within said interior opening, means yieldably holding the shaped plug in a position to gently press the facing material as the sealing head is lowered, a suction cup within the concave interior of each pocket member and movably associated therewith, means for lifting said suction cups relative to said frame to enable said suction cups to engage the undersides of said shells prior to upward movement of said frame, movable side plates on said sealing head for clamping against the pocket members to hold the facing material in position and seal the interior of the pocket members, and vacuum passages in said pocket member extending to the concave interior as well as to locations at both sides of said ribs.

4. A machine as defined in claim 1 wherein said means at the slitting station comprises: a plate on which said facing material rests, a frame overlying said plate, means for moving said frame toward and away from said plate, a stripper plate yieldably mounted on and below said frame for pressing said facing material against said plate, a pair of transversely reciprocable knife carriers on said frame having a plurality of depending knives, elongate slots in said stripper plate and plate to permit said knives to pass through the facing material captured therebetween, and means for reciprocating said knife carriers to move said knives along said elongate slots and make said less than full-width cuts.

5. A machine as defined in claim 4 including a plurality of headed rods extending up from said stripper plate and movably guided on said frame, and spring means urging said stripper plate downwardly whereby the stripper plate can engage said facing material in advance of said knives and can remain on the facing material as the knives are moved upwardly by initial upward movement of the frame.

6. A machine for manufacturing a disposable absorbent continence pad comprising, a formed shell with a pocket and covered with facing material, a sealing station, a vertically movable frame at said sealing station, a series of pocket members carried on said frame and each having a concave interior to receive a molded shell of the continence pad, and a pair of spaced-apart ribs, a vertically movable seal head overlying said pocket members, a plurality of seal members depending from said seal head and having perimeters shaped to coact with the pocket members and said ribs to press the facing material against the perimeter of the formed shells, each of said seal members having an interior opening, a shaped-plug within said interior opening, means yieldably holding the shaped-plug in a position to gently press the facing material as the sealing head is lowered, a suction cup within the concave interior of each pocket member and movably associated therewith, means for lifting said suction cups relative to said frame to enable said suction cups to engage the undersides of said shells prior to upward movement of said frame, movable side plates on said sealing head for clamping against the pocket members to hold the facing material in position and seal the interior of the pocket members, and vacuum passages in said pocket member extending to the concave interior as well as to locations at both sides of said ribs.

7. A machine for manufacturing a disposable absorbent continence pad comprising, means for indexing a web of thermoplastic material through a series of stations including a shell-forming station, means at said shell-forming station for molding a series of shells with compound curved side walls in said web of thermoplastic material with each shell having a pocket, a stuffing station where the pockets can be filled with a filler of fibrous absorbent material, a sealing station, a slitting station in advance of the sealing station through which a length of facing material travels to a position overlying said shells, said facing material being stretchable transverse to its length but not lengthwise thereof, means at the slitting station for making less than full-width transverse cuts in the facing material to form slits which will overlie said web at locations between shells at said sealing station to enable the facing material to adjust to the shape of the shells without wrinkling and without any cuts in the facing materials which overlies the absorbent material, and means at the sealing station for sealing said facing material to the perimeter including the side walls of said shells.

8. A machine as defined in claim 7 wherein said means at the shell-forming station comprises a lower vertically-movable frame having a series of concave molds with spaced raised ribs, a vertically-movable box overlying said frame, means on said vertically-movable box for coaction with said molds to shape the perimeter of the shells, means for moving said frame and box to bring said box into sealing relation with said molds, means for drawing a vacuum through portions of said molds where the middle parts of the shells are formed to assist in holding said thermoplastic material and adjacent said ribs, a series of plugs movably mounted on said box overlying said molds, means for lowering said plugs into the molds to conform the thermoplastic material into the molds, passages in said box for delivery of air under pressure downwardly around said plugs to assist in conforming the plastic material, and separate and distinct passages in each of said molds, box and plugs for chilled liquid which can be at different temperatures in each of said passages to remove heat from said thermoplastic material to set the shape of the shells.

9. A machine for manufacturing a disposable absorbent continence pad comprising, means for indexing a web of thermoplastic material through a series of stations including a shell-forming station, means at said shell-forming station for molding a series of shells in said web of thermoplastic material with each shell having a pocket, a stuffing station where the pockets can be filled with a filler of fibrous absorbent material, a sealing station, a slitting station in advance of the sealing station through which a length of facing material travels to a position overlying said shells, said facing material being stretchable transverse to its length but not lengthwise thereof, means at the slitting station for making less than full-width cuts in the facing material to form slits which will overlie said web at locations between shells at said sealing station to enable the facing material to adjust to the shape of the shells without wrinkling, means at the sealing station for sealing said facing material to the perimeter of said shells, a vertically movable frame, a series of pocket members carried on said frame and each having a concave interior to receive a molded shell, a vertically movable seal head overlying said pocket members, a plurality of seal members depending from said seal head and having perimeters shaped to coact with the pocket members to press the facing material against the perimeter of the formed shells, a suction cup within the concave interior of each pocket member and movably associated therewith, means for lifting said suction cups relative to said frame to enable said suction cups to engage the undersides of said shells prior to upward movement of said frame, and vacuum passages in said pocket member extending to the concave interior.

10. A machine for manufacturing disposable absorbent continence pads having a molded shell and a cover of facing material and having means at a sealing station comprising, a vertically movable frame, a series of pocket members carried on said frame and each having a concave interior to receive a molded shell, a vertically movable seal head overlying said pocket members, a plurality of seal members depending from said seal head and having perimeters shaped to coact with the pocket members to press the facing material against the perimeter of the formed shells, each of said seal members having an interior opening, a shaped plug within said interior opening, means yieldably holding the shaped plug in a position to gently press the facing material as the sealing head is lowered, and movable side plates on said sealing head for clamping against the pocket members to hold the facing material in position and seal the interior of the pocket members.

11. A machine for manufacturing disposable absorbent continence pads having a molded shell and a cover of facing material and having means at a sealing station comprising, a vertically movable frame, a series of pocket members carried on said frame and each having a concave interior to receive a molded shell, a vertically movable seal head overlying said pocket members, a plurality of seal members depending from said seal head and having perimeters shaped to coact with the pocket members to press the facing material against the perimeter of the formed shells, each of said seal members having an interior opening, a shaped-plug within said interior opening, means yieldably holding the shaped-plug in a position to gently press the facing material as the sealing head is lowered, and vacuum means for seating and holding the molded shells in the pocket members.

12. The method of making a disposable absorbent continence pad having a pre-formed shape for conformance with the body of a wearer including a shell with a curved bottom wall and compound curved side walls defining a pocket to hold a fibrous absorbent material and a fluid-transmitting facing material sealed to the perimeter of the shell to enclose the fibrous absorbent material in the shell comprising, molding a plurality of said shells at a shell-forming station, inserting the fibrous absorbent material in said shells at a stuffing station, advancing a web of said facing material to a slitting station, slitting said facing material at spaced locations along the length thereof at said slitting station to form a series of transverse slits, and sealing said facing material to said shells at a sealing station with the slits in the facing material disposed between successive shells to completely seal the absorbent material in the shell and permit the facing material to adjust to the shape of the shell.

13. The method of making a disposable absorbent continence pad having a preformed shape for conformance with the body of a wearer including a shell with a curved bottom wall and compound curved side walls defining a pocket to hold a fibrous absorbent material and a fluid-transmitting facing material sealed to the perimeter of the shell to enclose the fibrous absorbent material in the shell comprising, advancing a length of thermoplastic foam material in a series of index steps through a plurality of successive stations, heating said foam material at a heating station, molding a plurality of said shells at a shell-forming station, inserting the fibrous absorbent material in said shells at a stuffing station, advancing a web of said facing material to a slitting station through which said shells pass without work being performed thereon, slitting said facing material at spaced locations along the lengths thereof at said slitting station to form a series of transverse slits between sections of facing material which are to overlie the shell, and sealing said facing material to said shells at a sealing station with the slits in the facing material disposed between successive shells to permit the facing material to adjust to the shape of the shell.

* * * * *